United States Patent
Prisco

(10) Patent No.: US 8,395,342 B2
(45) Date of Patent: Mar. 12, 2013

(54) MEDICAL ROBOTIC SYSTEM ADAPTED TO INHIBIT MOTIONS RESULTING IN EXCESSIVE END EFFECTOR FORCES

(75) Inventor: Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 159 days.

(21) Appl. No.: 12/894,337

(22) Filed: Sep. 30, 2010

(65) Prior Publication Data

US 2011/0040306 A1    Feb. 17, 2011

Related U.S. Application Data

(63) Continuation of application No. 12/058,882, filed on Mar. 31, 2008, now Pat. No. 7,843,158.

(51) Int. Cl.
*A61B 17/04* (2006.01)

(52) U.S. Cl. .......... 318/566; 318/568.11; 318/628; 901/20

(58) Field of Classification Search .......... 318/565, 318/566, 568.11, 568.21, 628; 901/19, 20, 901/23
See application file for complete search history.

(56) References Cited

U.S. PATENT DOCUMENTS

| | | | |
|---|---|---|---|
| 6,231,565 B1 * | 5/2001 | Tovey et al. | 606/1 |
| 6,969,385 B2 * | 11/2005 | Moreyra | 606/1 |
| 7,250,028 B2 | 7/2007 | Julian et al. | |
| 7,453,227 B2 | 11/2008 | Prisco et al. | |
| 2007/0018958 A1 | 1/2007 | Tavakoli et al. | |
| 2007/0173873 A1 * | 7/2007 | Ranucci et al. | 606/180 |
| 2008/0046122 A1 | 2/2008 | Manzo et al. | |
| 2008/0147090 A1 | 6/2008 | Seibold et al. | |
| 2009/0088775 A1 | 4/2009 | Swarup et al. | |

OTHER PUBLICATIONS

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.

* cited by examiner

*Primary Examiner* — Bentsu Ro

(57) ABSTRACT

A medical robotic system includes a surgical instrument, a robotic arm assembly, an input device, and a processor. The surgical instrument has an end effector and a sensor for sensing a force exerted by the end effector, and is operatively mounted on the robotic arm assembly. The processor is configured to receive commanded movement of the end effector from the input device, receive information of the force from the sensor, determine a reduced velocity of the commanded movement that would inhibit damage causing motion of the end effector, and control robotic manipulation of the surgical instrument in response to the commanded movement of the end effector while restricting the velocity of the commanded movement to the reduced velocity.

18 Claims, 13 Drawing Sheets

MEDICAL ROBOTIC SYSTEM ADAPTED TO INHIBIT MOTIONS RESULTING IN EXCESSIVE END EFFECTOR FORCES

The present application is a continuation of U.S. patent application Ser. No. 12/058,882 (filed Mar. 31, 2008, now U.S. Pat. No. 7,843,158 B2), which is incorporated by reference herein for all purposes.

FIELD OF THE INVENTION

The present invention generally relates to medical robotic systems and in particular, to a medical robotic system adapted to inhibit motions resulting in excessive end effector forces.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist so that when added to the motions of manipulators holding the surgical instruments, they allow at least six degrees of freedom of motion, which is comparable to or even greater than the natural motions of open surgery.

The da Vinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

The patient-side cart typically includes three or more robotic arm assemblies with corresponding slave manipulators for holding and manipulating medical devices such as surgical instruments and image capturing devices for performing and/or viewing a medical procedure at a surgical site within a patient. To manipulate these medical devices, the surgeon's console also includes input devices which may be selectively associated with the medical devices and their respective slave manipulators. Since the movements of the input devices and their associated medical devices are scaled, this allows the surgeon to perform intricate medical procedures with greater ease than conventional open surgery. Further, it may even allow the surgeon to perform medical procedures that are not even feasible using conventional open surgery techniques.

To perform a minimally invasive surgical procedure on a patient, one or more incisions are first made in the patient and cannulae inserted therein to gain access to a surgical site within the patient. Setup arms supporting the slave manipulators are then positioned so as to allow the slave manipulators to attach to respective of the cannulae. Surgical instruments engaged on the slave manipulators are then inserted into the cannulae and properly positioned and oriented in order to perform the procedure. A surgeon may then manipulate input devices which are coupled to the slave manipulators and their respective surgical instruments through one or more controllers to perform the medical procedure.

Although minimally invasive surgery enables keyhole access to many surgical sites while avoiding the loss of dexterity associated with earlier laparoscopic techniques, it still has the drawback compared to open surgery of reducing the surgeon's feeling of touch and of contact forces. During the performance of a medical procedure, however, it may be desirable to prevent a surgical instrument's end effector from exerting excessive force.

As an example, if the end effector is a gripper being used for suturing, a surgeon may need to tie a knot as hard as possible short of breaking the suture. This may be difficult to do if the surgeon cannot feel how much force he or she is applying against the suture. Thus, it would be desirable in such case to not only provide some mechanism to prevent the surgeon from inadvertently breaking the suture, but also to give the surgeon some warning when the applied force is getting too strong for the current application.

As another example, if the end effector is an atraumatic grasper used to retract tissue or an organ, a surgeon may need to provide sufficient retraction to clear the operating field while avoiding to pull too hard on the tissues and blood supply to the retracted organ. Thus, it would be desirable in such case to again provide some mechanism to prevent the surgeon from inadvertently damaging the tissue or organ being retracted.

Many approaches, going under the general name of force feedback systems, have been proposed in the scientific literature to reproduce on the input control devices the same forces experienced by the instrument end effectors. Unfortunately in practice such approaches all suffer from the general shortcoming of low fidelity and delayed reproduction of the slave force on the input devices. Moreover force feedback systems in the literature always offer some risk of producing uncontrolled motions such as system instabilities, depending on the properties of the contact at the end effector and input device sides, and therefore, may not be generally suited for medical applications.

OBJECTS AND SUMMARY OF THE INVENTION

Accordingly, one object of one or more aspects of the present invention is a control system and method implemented in a medical robotic system that prevents an end effector being robotically manipulated by an operator of the medical robotic system from moving in ways that would result in the end effector exerting excessive force during the performance of a medical procedure.

Another object of one or more aspects of the present invention is a control system and method implemented in a medical robotic system that warns a surgeon when motions that result in excessive forces are being performed by an end effector of a surgical instrument being robotically manipulated by the surgeon.

These and additional objects are accomplished by the various aspects of the present invention, wherein briefly stated, one aspect is a method for inhibiting damage causing commanded motions from being performed by an end effector of a robotically manipulated surgical instrument, comprising: receiving commanded movement of the end effector; receiving information of force being exerted by the end effector; determining a reduced velocity of the commanded movement that would inhibit damage causing forces; and controlling the robotic manipulation of the surgical instrument in response to the commanded movement of the end effector so as to restrict the velocity of the commanded movement to the reduced velocity.

Another aspect is a medical robotic system, comprising: an input device; a robotic arm assembly; a surgical instrument operatively coupled to the robotic arm assembly, the surgical instrument having an end effector and a sensor adapted to sense a force being exerted by the end effector; and a processor configured to receive commanded movement of the end effector from the input device, receive information of the force from the sensor, determine a reduced velocity of the commanded movement that would inhibit damage causing motions of the end effector, and control robotic manipulation of the surgical instrument in response to the commanded movement of the end effector while restricting the velocity of the commanded movement to the reduced velocity.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
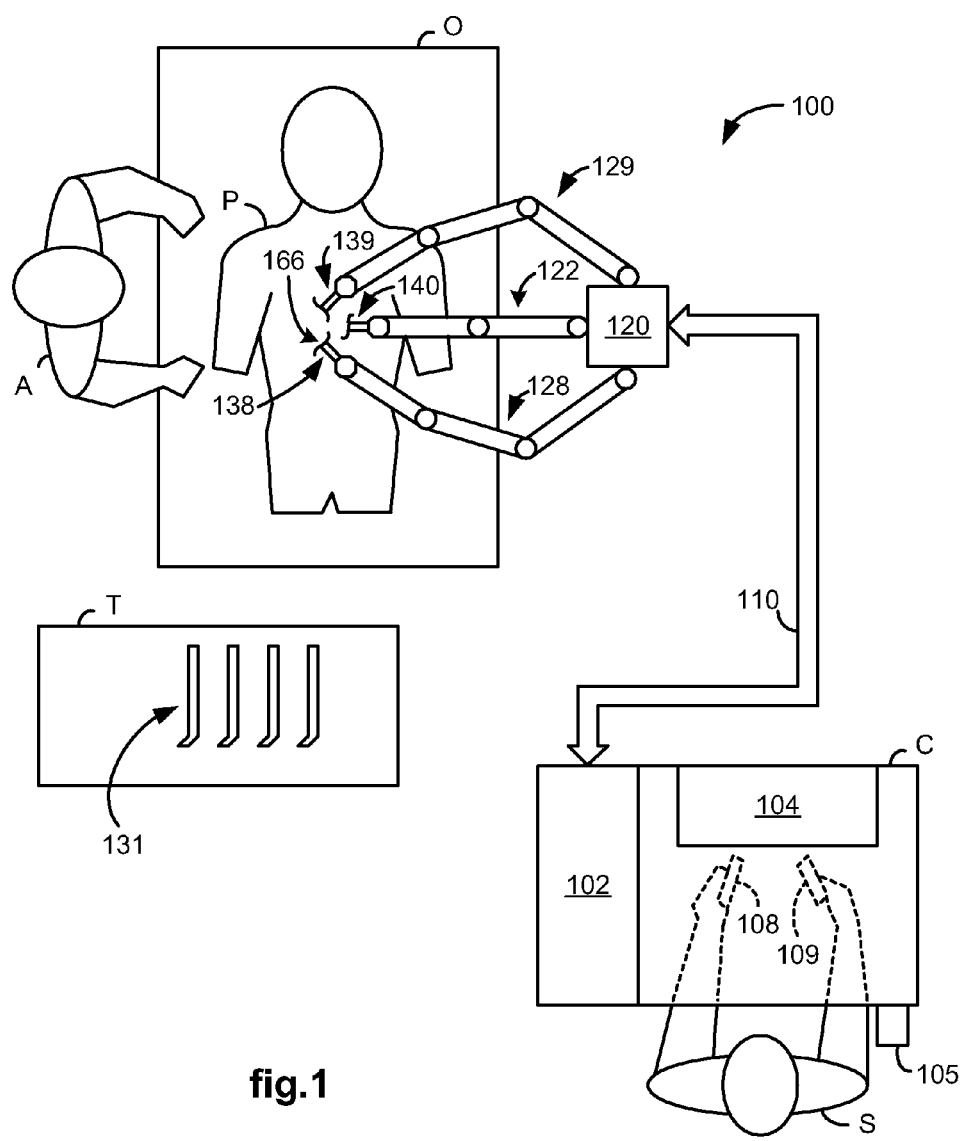
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is reclining on an Operating table ("O").

The Console includes a 3-D monitor 104 for displaying a 3-D image of a surgical site to the Surgeon, left and right manipulatable input devices 108, 109, a foot pedal 105, and a processor 102. The input devices 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the system 100.

The Surgeon performs a medical procedure by manipulating the input devices 108, 109 (also referred to herein as "master manipulators") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by a stereoscopic endoscope 140.

Each of the tools 138, 139, as well as the Endoscope 140, is conventionally inserted through a tool guide (such as 270 in FIG. 2) into the Patient so as to extend down to the surgical site through a corresponding minimally invasive incision such as incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the Assistant may remove the tool no longer being used from its robotic arm assembly, and replace it with another tool 131 from a Tray ("T") in the operating room.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices and their end effectors. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

The robotic arm assemblies 122, 128, 129 are mounted on a structure 120 which may be a patient-side cart or a ceiling mount.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of input devices 108, 109 to their respective slave manipulators of robotic arm assemblies 128, 129 through control signals over bus 110 so that the Surgeon can effectively manipulate their respective tools 138, 139. Another important function is to implement various control system processes and the methods as described herein. Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on the construction and operation of medical robotic systems such as described herein, see, e.g., U.S. Pat. No. 6,493,608 "Aspects of a Control System of a Minimally Invasive Surgical Apparatus," and U.S. Pat. No. 6,424,885 "Camera Referenced Control in a Minimally Invasive Surgical Apparatus," which are incorporated herein by reference.

Figure 2:
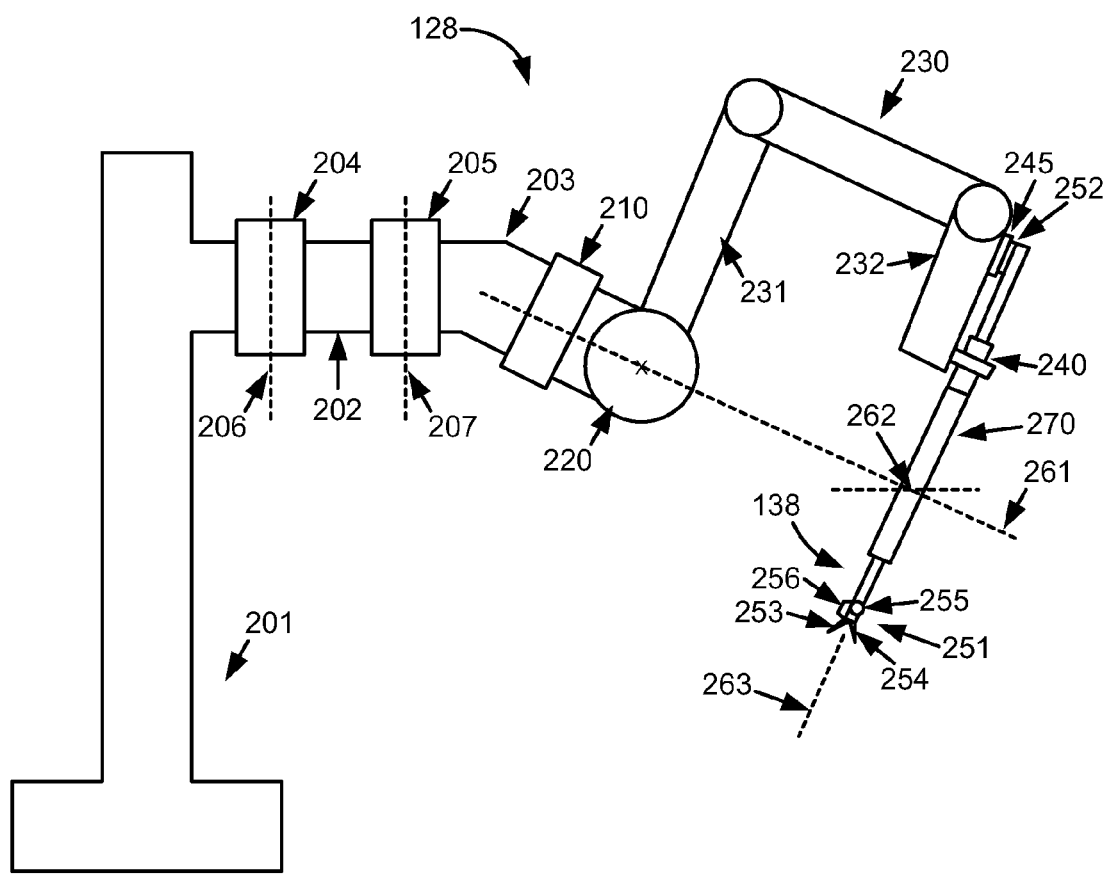
FIG. 2 illustrates a simplified side view of a robotic arm assembly that is usable with various aspects of the present invention.

FIG. 2 illustrates, as an example, a side view of a simplified (not necessarily in proportion or complete) version of the robotic arm assembly 128 (which is also representative of the robotic arm assemblies 122, 129) holding the surgical instrument 138 for performing a medical procedure. A tool guide 270 is inserted through the minimally invasive incision 166 in the patient, and coupled to the robotic arm assembly 128 by a guide holder 240. The surgical instrument 138 may then be inserted into the patient through the tool guide 270. The robotic arm assembly 128 is mechanically supported by a base 201, which may be part of a patient-side movable cart 120.

Links 202, 203 are coupled together and to the base 201 through horizontal setup joints 204, 205. The setup joints 204, 205 in this example are passive joints that allow manual positioning of the arm 128 when their brakes are released. For example, setup joint 204 allows link 202 to be manually rotated about axis 206, and setup joint 205 allows link 203 to be manually rotated about axis 207. This portion of the robotic arm assembly 128 including these passive joints is referred to herein as the setup arm.

Although only two links and two setup joints are shown in this example, more or less of each may be used as appropriate in this and other robotic arm assemblies in conjunction with the present invention. For example, although setup joints 204, 205 are useful for horizontal positioning of the arm 128, additional setup joints may be included and useful for limited vertical and angular positioning of the arm 128. For major vertical positioning of the arm 128, however, the arm 128 may also be slidably moved along the vertical axis of the base 201 and locked in position.

The robotic arm assembly 128 also includes two active joints and a number of gears driven by motors. A yaw joint 210 allows arm section 230 to rotate around an axis 261, and a pitch joint 220 allows arm section 230 to rotate about an axis perpendicular to that of axis 261 and orthogonal to the plane of the drawing. The portion of the robotic arm assembly 128 including these active joints and motor driven gears is referred to herein as the slave manipulator.

The arm section 230 is configured so that sections 231, 232 are always parallel to each other as the pitch joint 220 is rotated by its motor. As a consequence, the instrument 138 may be controllably moved by driving the yaw and pitch motors so as to pivot about the pivot point 262, which is generally located through positioning of the setup joints 204, 205 so as to be at the point of entry into the patient. In addition, the surgical instrument 138 is coupled to a carriage 245 on the arm section 230 which in turn is coupled to a linear drive mechanism to extend or retract the instrument 138 along its insertion axis 263. An interface 252 including mating parts of the motor driven gears on the carriage 245 and a proximal end of the instrument 138 to drive a three degree-of-freedom (e.g., pitch, roll and yaw) wrist mechanism 255 and other drivable members such as jaws 253, 254 of an end effector 251 of the instrument 138 using conventional gear, pulley and cable arrangements, as well as rotation of a shaft of the instrument 138 so as to provide roll angular movement of the instrument 138 about its insertion axis 263.

Although each of the yaw joint 210, pitch joint 220 and motor driven gears in the carriage 245 is controlled by an individual joint or gear controller, the controllers may be controlled by a common master/slave control system so that the slave manipulator of the robotic arm assembly 128 may be controlled through user (e.g., surgeon or operator) manipulation of its associated master manipulator.

A multi-component force sensor 256 is provided to sense forces being exerted by the end effector 251, such as pulling forces exerted during a suturing process. Although shown as being on or near the tip of the surgical instrument 138, an appropriate force sensor may also or instead be mounted on the arm section 232, or other suitable point on the arm 128, where forces exerted by the end effector 251 may be sensed. Torque sensors that sense motor torques which are used to drive joints to desired joint positions, such as joints in the wrist mechanism 255, may also be used after conventional processing to determine forces exerted by the end effector 251.

Figure 3:
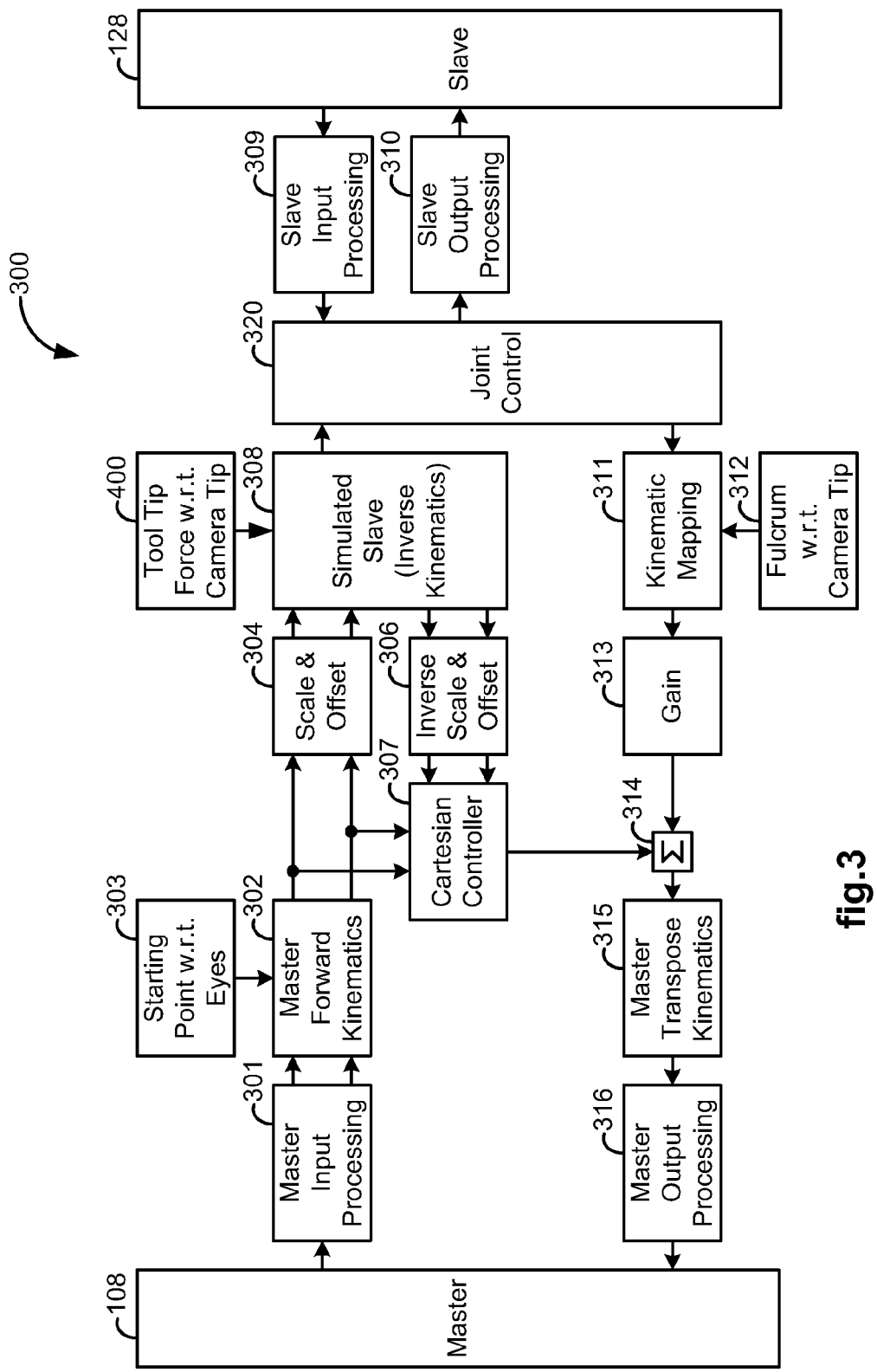
FIG. 3 illustrates a block diagram of a master/slave control system utilizing aspects of the present invention.

FIG. 3 illustrates, as an example, a block diagram of a master/slave control system 300 for controlling movement of the slave manipulator of the robotic arm assembly 128 and consequently, the position and orientation of its attached tool 138, as commanded by movement of the master manipulator 108 by the Surgeon. A similar control system may also be provided for the slave manipulator of the robotic arm assembly 129 and its associated master manipulator 109.

Both the master and slave manipulators include a number of linkages connected by joints so as to facilitate multiple degrees-of-freedom movement. As the Surgeon moves the master manipulator 108 from one position to another during the course of performing a surgical procedure, sensors associated with the master manipulator joints provide information indicating such command movement in master joint space, and sensors associated with the slave manipulator joints provide information indicating slave manipulator and consequently, tool 138 movement in slave joint space for feedback purposes.

A master input processing unit 301 receives the information of the master joint positions, which are sampled at the control system processing rate (e.g., 1300 Hz in the present example), from the master joint sensors in the master manipulator 108, and computes joint velocities from the sensed joint positions. A master forward kinematics processing unit 302 receives the master joint positions and velocities from the master input processing unit 301, transforms them from master joint space to corresponding positions and velocities of the master frame (i.e., the frame associated with the master manipulator 108) in Cartesian space relative to the eye reference frame (i.e., the reference frame associated with the position of the surgeon's eyes), using, for example, a Jacobian matrix and eye related information separately determined and provided in block 303.

A scale and offset processing unit 304 receives the Cartesian position and velocity commands from the master forward kinematics processing unit 302, scales the commanded movement according to a scale factor selected to perform the surgical procedure, and takes into account offsets to generate desired slave tool frame (i.e., the frame associated with the tool 138) positions and velocities. For economy of words, Cartesian position is to be interpreted to include Cartesian orientation in this specification where appropriate. The scale adjustment is useful where small movements of the slave manipulator of the robotic arm assembly 128 are desired relative to larger movement of the master manipulator 108 in order to allow more precise movement of the slave tool 138 at the surgical site. The offsets, on the other hand, determine, for example, the corresponding position and/or orientation of an end effector frame (e.g., the frame associated with an end effector of the tool 138) in the camera reference frame (i.e., the frame associated with the distal tip of the endoscope 140) relative to a position and orientation of the master frame in the eye reference frame.

A simulated slave processing unit 308 (also referred to as a "simulated domain") receives desired slave tool frame position and velocity commands from the scale and offset processing unit 304, and limits the desired slave tool frame position, orientation and velocities, to assigned Cartesian limits for instance to enforce correct and intuitive operation of the tool 138 by keeping it within its dexterous workspace and to prevent motions that would result in excessive forces being exerted by the end effector 251 of the surgical instrument 138 mounted on the robotic arm assembly 128. The simulated slave processing unit 308 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function to that of the scale and offset processing unit 304 on them. A Cartesian controller 307 receives as first inputs, the inputs to the scale and offset processing unit 304 and as second inputs, the outputs of the inverse scale and offset processing unit 306. The Cartesian controller 307 then generates an error signal as a difference of the first and second inputs, and a Cartesian force "$F_{CART}$" from the error signal such as with the following formula:

$$F_{CART} = K(\Delta x) + B(\Delta \dot{x}) \tag{1}$$

where "K" is a spring constant, "B" is a damping constant, "$\Delta \dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

A master transpose kinematics processing unit 315 receives the Cartesian force $F_{CART}$ through a summation node 314, and generates a corresponding torque in joint space using, for example, the Jacobian transpose matrix and kinematic relationships associated with the master manipulator 108. A master output processing unit 316 receives the master torque signals from the master transpose kinematics processing unit 315, generates electrical currents corresponding to the master torque signals, and supplies the electrical currents to corresponding master joint motors of the master manipulator 108. As a result, a surgeon operating the master manipulator 108 feels the Cartesian force, $F_{CART}$, whenever the surgeon is commanding a position or velocity which exceeds system Cartesian or slave joint limits, or would result in a kinematic singularity condition for the slave manipulator of the robotic arm assembly 128.

As the master input processing unit 301 is receiving master joint positions from sensors in the master manipulator 108, a slave input processing unit 309 is also receiving slave joint positions from position sensors in the slave manipulator at the control system processing rate. A joint control unit 320 receives the slave joint positions from the slave input processing unit 309 and the simulated joint position commands provided from the simulated slave processing unit 308, and generates slave torque command signals for the slave joint motors and master torque feedback command signals for the master joint motors.

The slave torque command signals are generated by the joint control unit 320 so as to drive joints of the slave manipulator until feedback errors calculated in the joint control unit 320 zero out. A slave output processing unit 310 receives the slave torque command signals from the joint control unit 320, converts them into appropriate electrical currents, and supplies the electrical currents to the joint motors of the slave manipulator so as to drive the motors accordingly.

The master torque feedback command signals are generated by the joint control unit 320 as a function of the slave joint position and velocity tracking errors so as to reflect forces being exerted against the tool 138 or its slave manipulator back to the master manipulator 108 so that they may be felt by the Surgeon. A kinematic mapping unit 311 receives the master torque feedback command signals from the joint control unit 320, and generates the corresponding Cartesian force at the tip of the tool 138 relative to the camera frame of the endoscope 140 using the slave kinematic configuration and the previously calculated slave fulcrum (e.g., pivot point) position information provided in block 312.

A gain 313 adjusts the magnitude of the Cartesian force so as to ensure system stability while providing adequate force sensation to the Surgeon. The gain adjusted Cartesian force is then passed through the summation node 314, and processed along with the Cartesian force provided by the Cartesian controller 307 through the master transpose kinematics processing unit 315 and master output processing 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave fulcrum information provided in block 312, which are based upon well-known mathematics, are described, for example, in previously incorporated by reference and U.S. Pat. No. 6,424,885, "Camera Referenced Control in a Minimally Invasive Surgical Apparatus."

The joint control unit 320 includes a joint controller for each active joint and gear of the slave manipulator of the robotic arm assembly 128 that is being controlled by the master/slave control system 300. In particular, where the slave manipulator 128 includes a yaw joint 210, a pitch joint 220, and an insertion axis gear 245, such as the robotic arm assembly 128 of FIG. 2, each of these joints or gears will have its own controller. To simplify the description herein and in the claims, the term "joint" is to be understood as a connection (translational or revolute) between two links, and may include gears as well as any other controllable component coupled to linear drive mechanisms that may be used in controlling robotic arm assemblies.

As previously mentioned, the simulated slave processing unit 308 prevents motions that would result in excessive forces being exerted by the end effector 251 of the surgical instrument 138 mounted on the robotic arm assembly 128. To do so, it receives information of the force being exerted by the end effector from block 400 as well as the desired slave tool frame position and velocity commands that it receives from the scale and offset processing unit 304.

Figure 4:
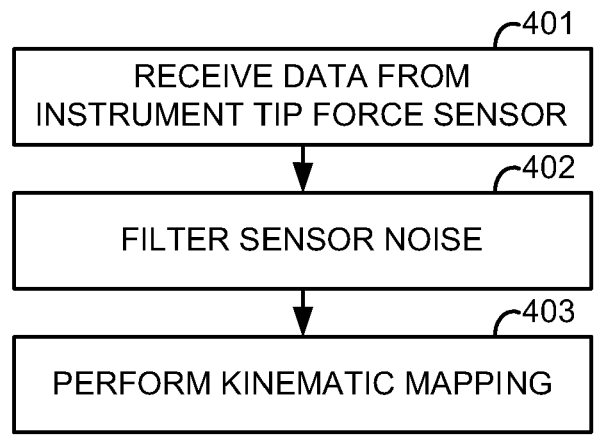
FIG. 4 illustrates a flow diagram of a method for generating a Cartesian force with respect to a camera tip for use with a master/slave control system utilizing aspects of the present invention.

FIG. 4 illustrates, as an example, a flow diagram of a method implementing block 400 in the processor 102 to generate a Cartesian force with respect to the image reference frame (i.e., camera tip) from a sensed force exerted by the end effector 251 of the surgical instrument 138. In 401, data is received from the force sensor 256 which senses a force being exerted by the end effector 251 of the surgical instrument 138. In 402, sensor noise is filtered out of the data, and in 403, the filtered data is processed by applicable kinematic mapping so that the Cartesian force "F" with respect to the image reference frame is generated.

Three alternative embodiments for the simulated slave processing unit 308 are described hereinbelow. FIGS. 5-8 illustrate a first embodiment in which velocity limiting to prevent motions that would result in excessive forces being exerted on the end effector is performed in a Cartesian velocity limiter 600. FIGS. 9-15 illustrate the second and third embodiments in which the Cartesian velocity limiter 600 is omitted and velocity limiting to prevent motions that would result in excessive forces being exerted on the end effector is performed in a simulator 1000 and more particularly, in a joint position and velocity limiter block 1100 included in the simulator 1000, which receives velocity limits from a velocity limit generator (i.e., 1200 for the second embodiment as described in reference to FIGS. 12-13 and 1200' for the third embodiment as described in reference to FIGS. 14-16) that is also included in the simulator 1000.

Figure 5:
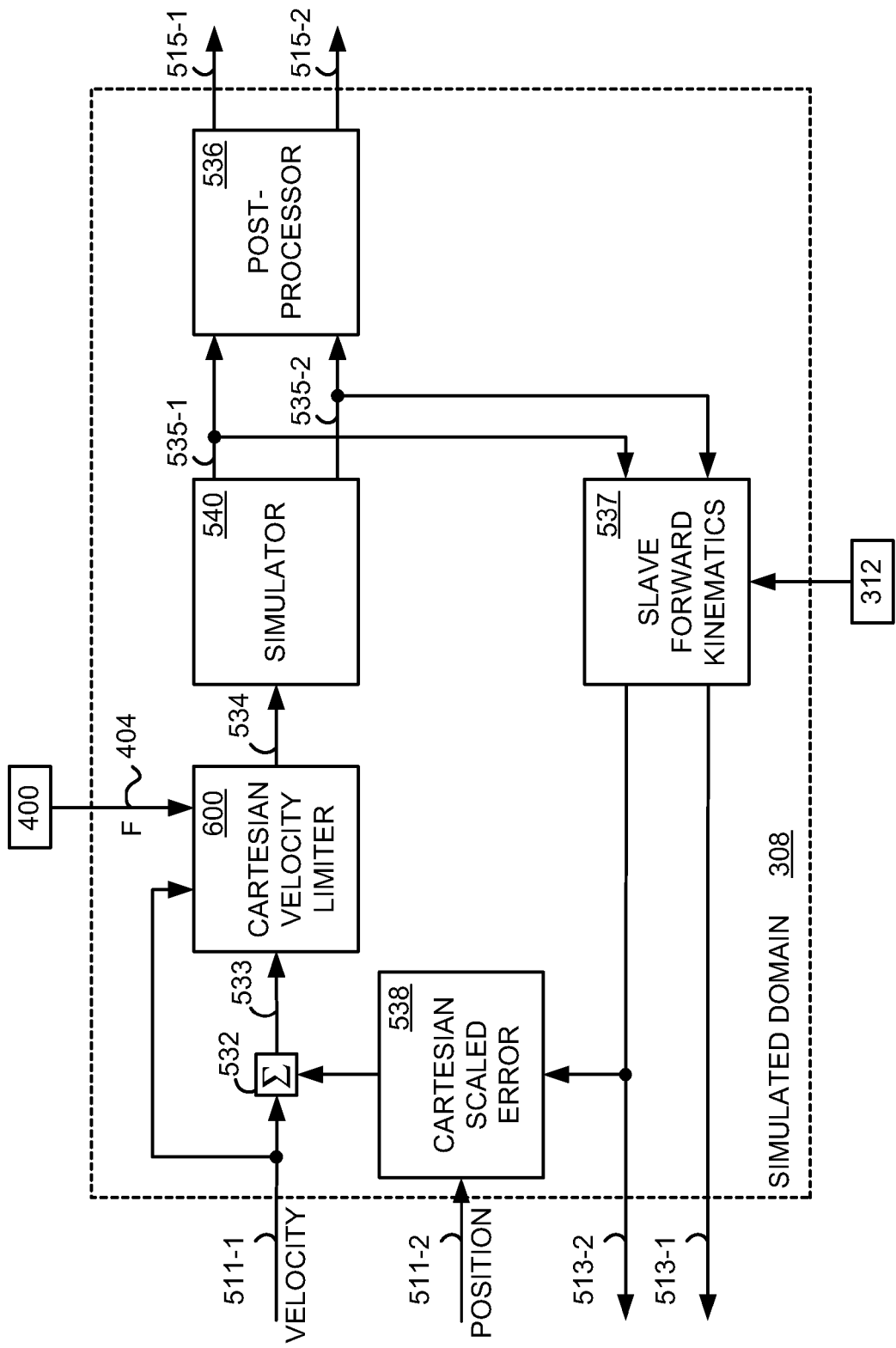
FIG. 5 illustrates a block diagram of a first simulated domain block included in a master/slave control system utilizing aspects of the present invention.

FIG. 5 illustrates, as an example, a block diagram of a first embodiment of the simulated slave processing unit 308. The desired Cartesian velocity (identified here as 511-1) is received from the scale and offset processing unit 304 and passed to a summation junction 532. It is to be appreciated that the desired Cartesian velocity 511-1 represents a stream of digital values over time (also referred to herein as a "signal") that is received and passed to the summation junction 532 sequentially at the processing rate of the control system, which is 1300 Hz in the present example.

At the junction 532, an error signal is imparted on the desired Cartesian velocity 511-1 (e.g., the commanded velocity at current time "$t_k$") when the value of a prior desired Cartesian velocity (e.g., the commanded velocity at prior time "$t_{k-1}$") would have instructed the simulated slave 308 to transgress one or more limitations. If the prior desired Cartesian velocity would not have caused a transgression, only a small error signal due to numerical precision is generated and the current desired Cartesian velocity 511-1 passes through the summation junction 532 basically unchanged as far as the operator of the system is concerned. The velocity signal passed from the summation junction 532 is referred to as a Cartesian reference velocity and indicated by arrow 533.

From the summation junction 532, the Cartesian reference velocity 533, the desired Cartesian velocity 511-1 and the Cartesian force "F" 404 (generated by block 400) are fed to a Cartesian velocity limiter 600 which limits the Cartesian reference velocity 533 so as to prevent, or at least inhibit, motions that would lead to excessive forces being exerted by the end effector 251 of the surgical instrument 138, as further described below in reference to FIGS. 6-7. The output of the Cartesian velocity limiter 600 is a limited Cartesian reference velocity 534 that is provided to a simulator 540.

In the simulator 540, the limited Cartesian reference velocity 534 is processed by a modified Jacobian inverse controller that is adapted to inhibit the detrimental effects which result when a singularity is approached and convert the limited Cartesian reference velocity 534 to a resulting joint velocity. The resulting joint velocity is integrated in the simulator 540 to yield a corresponding resulting joint position. The resulting joint velocity and position are each checked in the simulator 540 to determine whether either of them would transgress a limitation. If they would not, then they pass through the simulator 540 unchanged as a simulated joint velocity 535-1 and simulated joint position 535-2. On the other hand, if they would, then the resulting joint velocity and position are limited as necessary so as not to transgress their respective limitations and the thus limited versions of the resulting joint velocity and joint position pass through the simulator 540 as the simulated joint velocity 535-1 and simulated joint position 535-2.

A post-processor 536 receives the simulated joint velocity 535-1 and position 535-2 from the simulator 540, modifies them to filter out undesirable frequency characteristics such as tremors resulting from inadvertent shaking of the master control 108 by the hand of the surgeon and resonance frequencies associated with the robotic arm assembly 128, and generates corresponding physical slave joint velocity 515-1 and position 515-2 commands that may be used to drive the slave manipulator of the robotic arm assembly 128 as described in reference to FIG. 3.

A slave forward kinematics block 537 also receives the simulated joint velocity 535-1 and position 535-2 from the simulator 540 along with the Cartesian coordinate values of the slave manipulator position relative to the camera frame as provided from block 312 to compute a corresponding feedback Cartesian velocity 513-1 and position 513-2 which are provided to the inverse scale and offset block 306 for processing as described in reference to FIG. 3.

The feedback Cartesian position 513-2 is also provided to a Cartesian scaled error block 538 along with the desired Cartesian position 511-2 which was generated and provided by the Scale and offset block 304. The two position signals 513-2, 511-2 are compared at 538 to compute an error signal should they not correspond. Should the two position signals 513-2, 511-2 be equal, namely where the desired Cartesian velocity signal 511-1 was not restricted in the simulated domain 308, no error signal is generated apart from potentially a small numerical error.

In the case where the desired Cartesian velocity 511-1 was restricted in the simulated domain 308, the simulated joint velocity 535-1 would not correspond with the desired Cartesian velocity 511-1 that is input to the simulated domain 308. Accordingly, after integration in the simulator 540 and conversion to Cartesian space by the slave forward kinematics block 537, the feedback Cartesian position 513-2 would not correspond with the original desired Cartesian position 511-2. Consequently, an error of a magnitude determined typically by subtraction of the feedback Cartesian position 513-2 from the desired Cartesian position 511-2 and multiplication with an appropriate constant is generated by the Cartesian scaled error block 538. This error is imposed on the next desired Cartesian velocity 511-1 at the summation junction 532.

Figure 6:
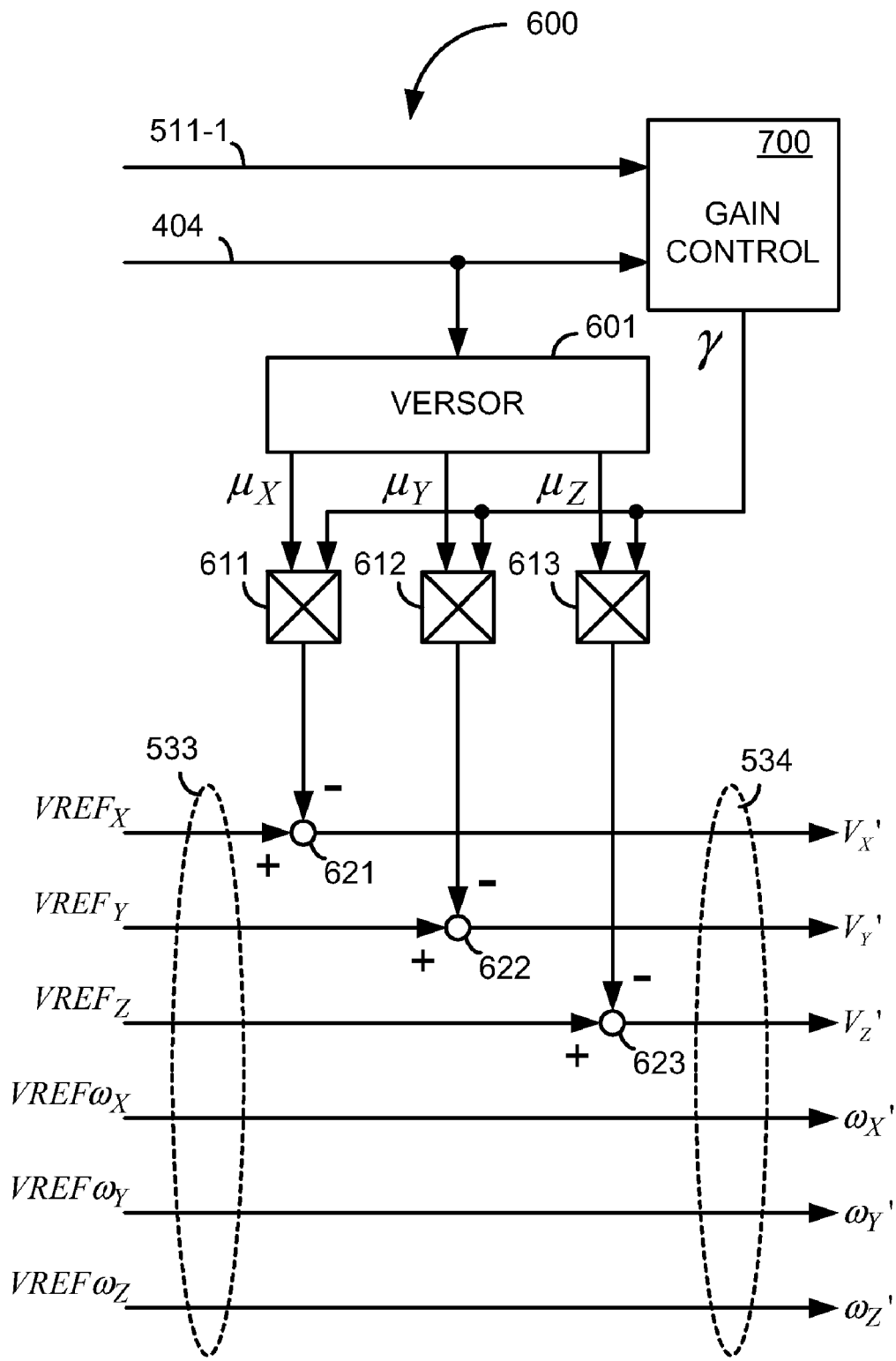
FIG. 6 illustrates a block diagram of a velocity limiter included in the first simulated domain block, utilizing aspects of the present invention.

FIG. 6 illustrates, as an example, a block diagram of the Cartesian velocity limiter 600. The purpose of the Cartesian velocity limiter 600 is to limit a component of the desired Cartesian velocity 511-1 and consequently, the reference velocity 533 in the direction of the force "F" 404 so as to prevent motions that would result in excessive forces being exerted by the end effector 251 of the surgical instrument 138.

Figure 7:
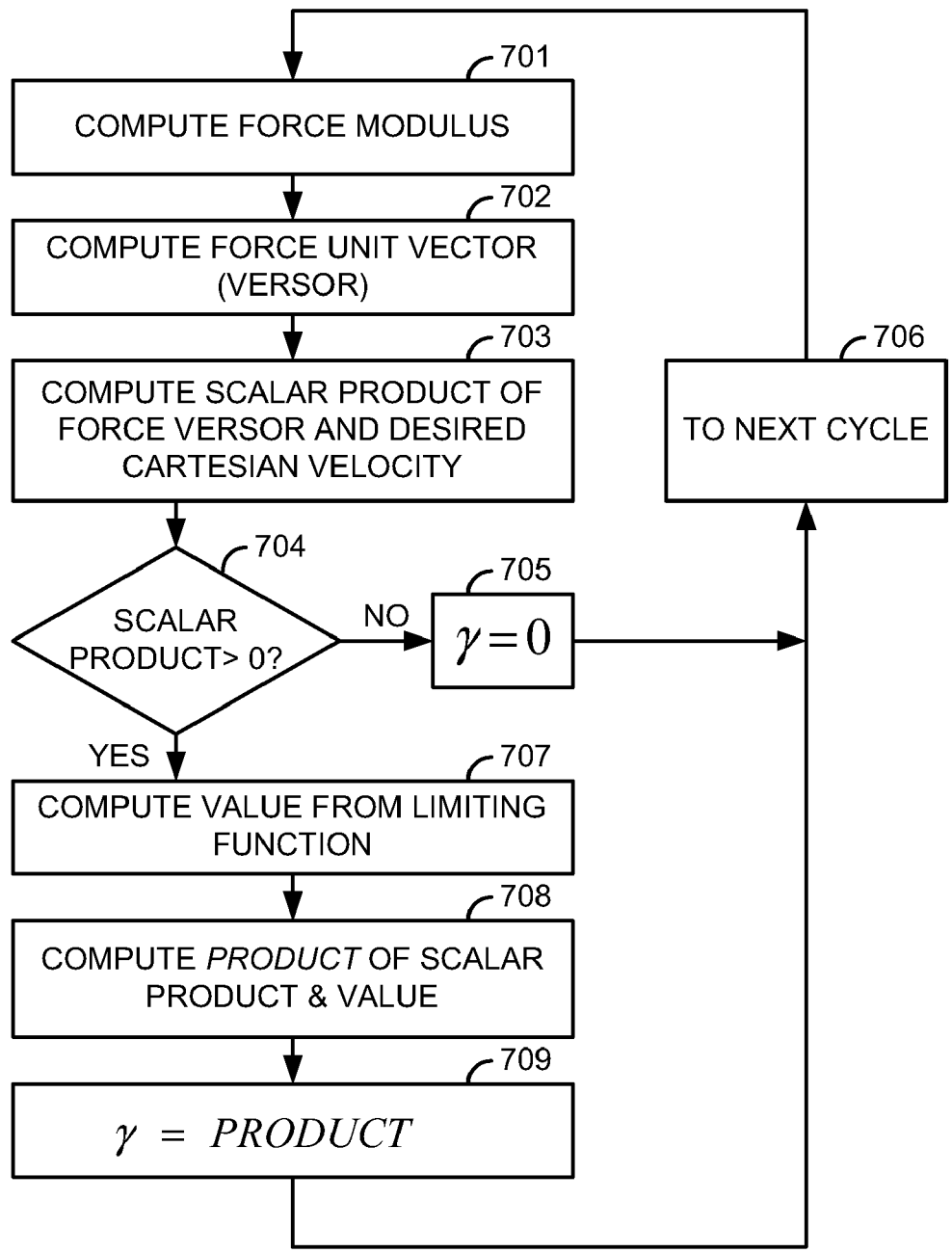
FIG. 7 illustrates a flow diagram of a method for generating a gain to be used in a velocity limiter included in the first simulated domain block, utilizing aspects of the present invention.

A gain control 700 generates a gain "γ" by processing the desired Cartesian velocity 511-1 and the Cartesian force 404 according to a method described in reference to FIG. 7. A versor block 601 calculates a force versor "$\vec{\mu}$" ($\mu_X$, $\mu_Y$, $\mu_Z$) as described in reference to 701-702 of FIG. 7. The generated gain "γ" is then provided along with components of the force versor "$\vec{\mu}$" ($\mu_X$, $\mu_Y$, $\mu_Z$) to respective multiplication blocks 611-613 to generate products (γ·$\mu_X$, γ·$\mu_Y$, γ·$\mu_X$). The products are then subtracted from respective components of the Cartesian reference velocity 533 (i.e., having components $V_X$, $V_Y$, $V_Z$, $\omega_X$, $\omega_Y$, $\omega_Z$) at nodes 621-623 to generate velocity inputs 534 (i.e., having components $V_X'$, $V_Y'$, $V_Z'$, $\omega_X'$, $\omega_y'$, $\omega_Z'$) to the simulator 540 according to the following equations:

$$V_X' = VREF_X - \gamma \cdot \mu_X \quad (2)$$

$$V_Y' = VREF_Y - \gamma \cdot \mu_Y \quad (3)$$

$$V_Z' = VREF_Z - \gamma \cdot \mu_Z \quad (4)$$

$$\omega_X' = \omega_X \quad (5)$$

$$\omega_Y' = \omega_Y \quad (6)$$

$$\omega_Z' = \omega_Z \quad (7)$$

FIG. 7 illustrates, as an example, a flow diagram of the method implemented in the gain control block 700 for generating the gain "γ" which is used in the Cartesian velocity limiter 600 as described in reference to FIG. 6. In 701, the magnitude of the force "F" 404 is calculated:

$$|\vec{F}| = \sqrt{F_X^2 + F_Y^2 + F_Z^2} \quad (8)$$

In 702, the force versor is calculated:

$$\vec{\mu} = \begin{pmatrix} \mu_X \\ \mu_Y \\ \mu_Z \end{pmatrix} = \begin{pmatrix} \frac{F_X}{|\vec{F}|} \\ \frac{F_Y}{|\vec{F}|} \\ \frac{F_Z}{|\vec{F}|} \end{pmatrix} \quad (9)$$

In 703, the scalar product of the force versor "$\vec{\mu}$" and desired Cartesian velocity "$\vec{V}$" 511-1 is calculated:

$$\langle \vec{V}, \vec{\mu} \rangle = V_X \mu_X + V_Y \mu_Y + V_Z \mu_Z \quad (10)$$

In 704, a determination is made whether the scalar product is greater than zero. If the determination in 704 is NO, then the desired Cartesian velocity 511-1 and the Cartesian force "F" are not pointing in the same direction and the motion is not threatening to increase the force. In particular, if the end effector is a gripper being used for suturing at the time, then there is no threat in such case of the gripper breaking the suture. Consequently, in 705, the gain "γ" is set to zero and provided to each of the gain blocks 601, 602, 603. The method then proceeds to 706 where it jumps back to 701 to process 701-709 for the next cycle.

Figure 8:
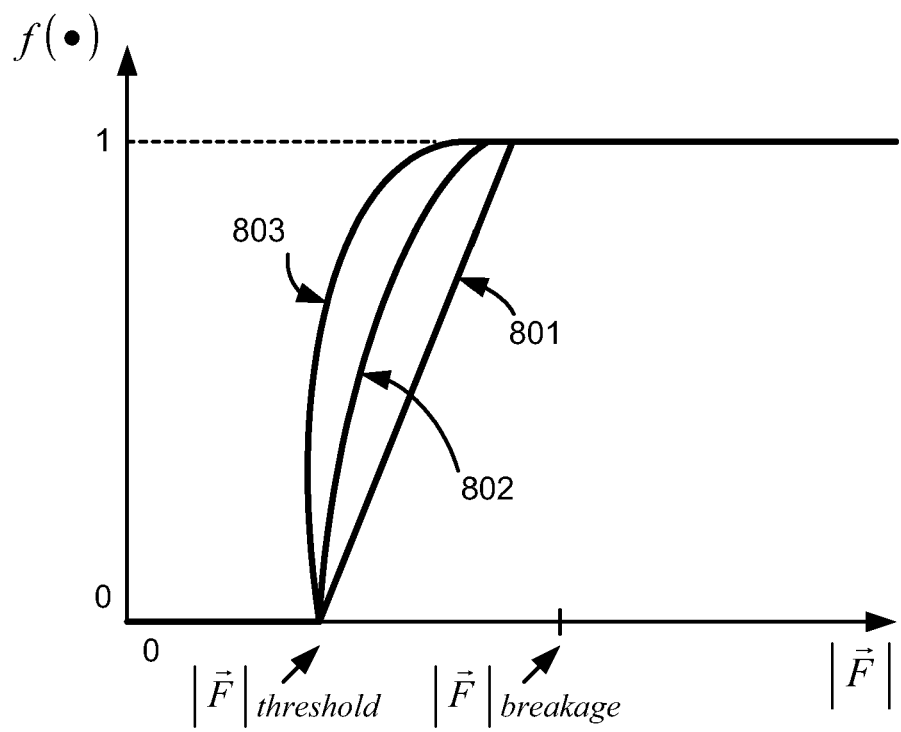
FIG. 8 illustrates exemplary functions useful in a method for performing gain control in the velocity limiter included in the first simulated domain block, utilizing aspects of the present invention.

On the other hand, if the determination in 704 is YES, then in 707, a value "f(·)" is computed from a velocity limiting function, such as one of the functions depicted in FIG. 8, wherein first, second, third velocity limiting functions 801, 802, 803 are each characterized by their values of "f(·)" being zero until the magnitude of the force $|\vec{F}|$ exceeds a threshold value $|\vec{F}|_{threshold}$. At that point, the value "f(·)" increases linearly for the first function 801, polynomially for the second function 802, and exponentially for the third function 803 to the value "1". For each function, the value "1" is reached before the magnitude of the force $|\vec{F}|$ reaches a breakage force $|\vec{F}|_{breakage}$ which corresponds to a force magnitude which would be considered excessive, such as the force that would break a suture. The type of function used (i.e., the first, second, third, or other velocity limiting function) depends on user preference. For example, some users may find the linear function 801 to be too slow at its transitions and therefore, they may prefer a more rapid transition towards a full stop such as offered by the polynomial and exponential functions 802, 803.

In 708, the product of the scalar product "$\langle \vec{V}, \vec{\mu} \rangle$" and the value "f(·)" is computed. In 709, the gain "γ" is set equal to the product computed in 708 and provided to each of the multiplication blocks 611, 612, 613. The method then proceeds to 706 where it jumps back to 701 to process 701-709 for the next cycle.

Note that in this first embodiment of the invention, after the magnitude of the force $|\vec{F}|$ exceeds the threshold value $|\vec{F}|_{threshold}$, then the translational velocity components ($VREF_X$, $VREF_Y$, $VREF_Z$) of the Cartesian reference velocity 533 are increasingly reduced as the magnitude of the force $|\vec{F}|$ increases until their components in the direction of the force "F" 404 are zeroed, which is to occur prior to the magnitude of the force $|\vec{F}|$ reaching a breakage force $|\vec{F}|_{breakage}$.

Figure 9:
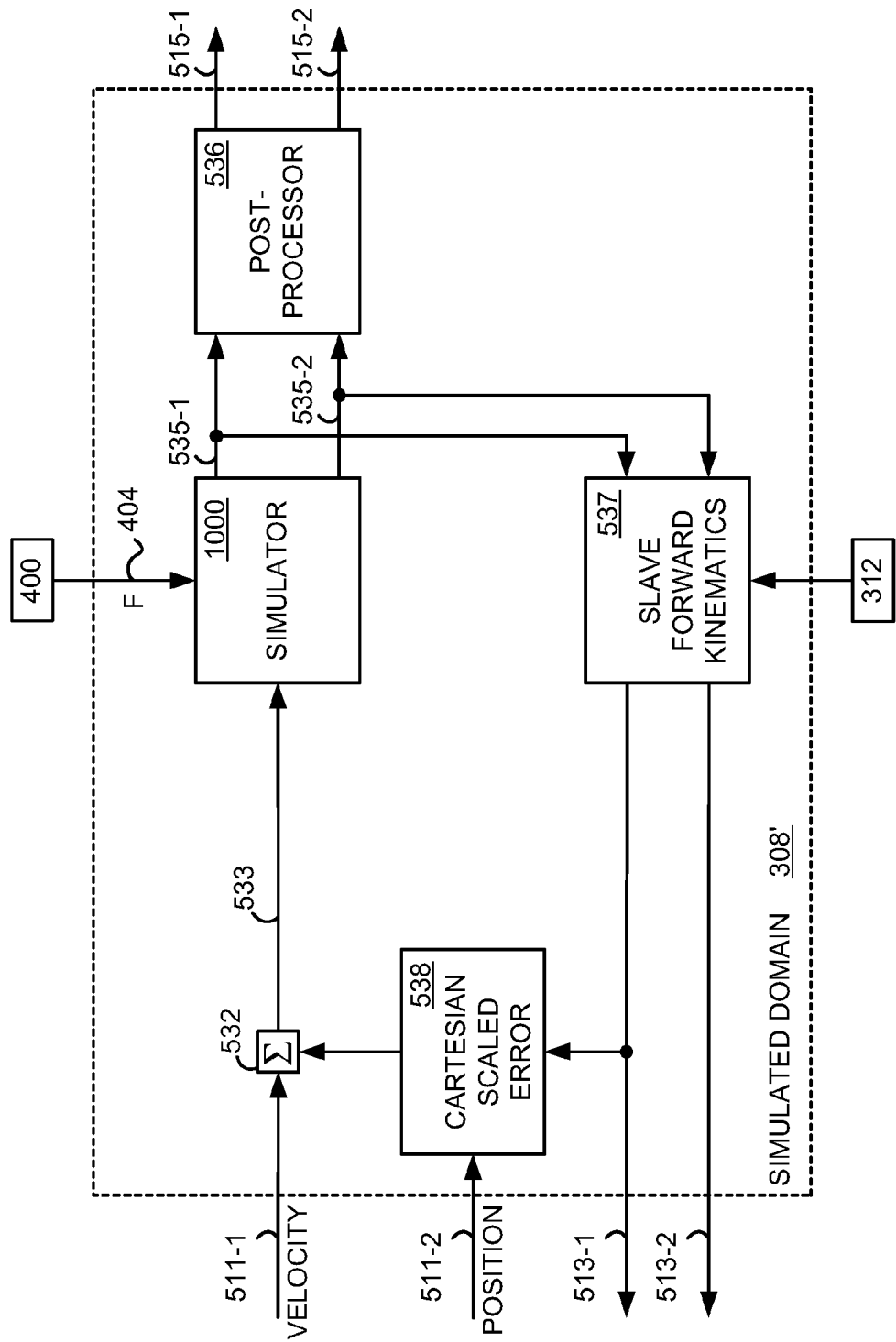
FIG. 9 illustrates a block diagram of a second simulated domain block included in a master/slave control system utilizing aspects of the present invention.

FIG. 9 illustrates, as an example, a block diagram of a second simulated domain block 308' which is used with the second and third embodiments of the invention. In the second simulated domain 308', the Cartesian velocity limiter 600 is eliminated and its velocity limiting function is performed instead in a simulator 1000. The post-processor 536, slave forward kinematics 537 and Cartesian scaled error 538, on the other hand, function the same as their like-referenced counterparts in the first simulated domain 308.

Figure 10:
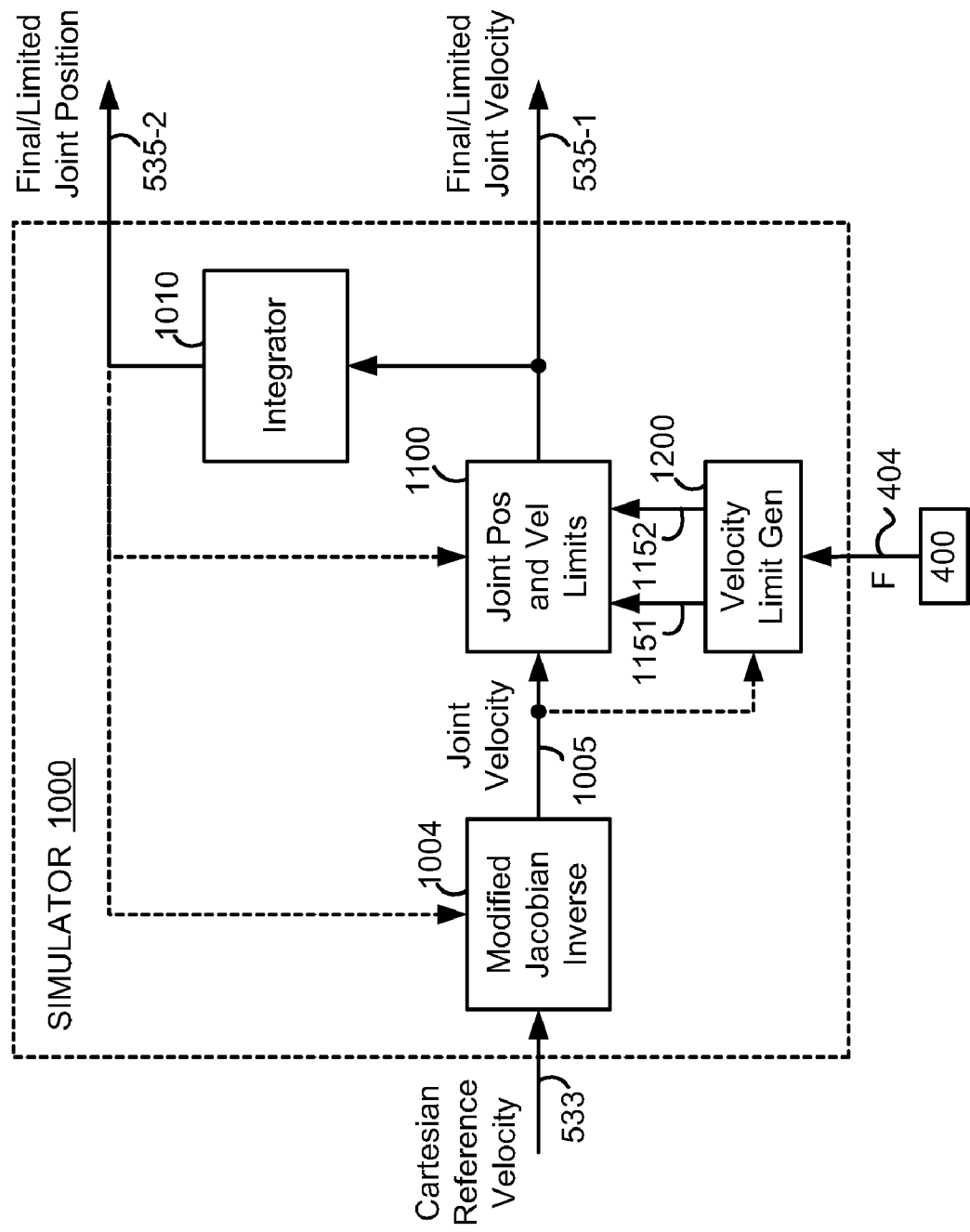
FIG. 10 illustrates a block diagram of a simulator included in the second simulated domain block, utilizing aspects of the present invention.

FIG. 10 illustrates, as an example, a block diagram of the simulator 1000 included in the second simulated domain block 308'. A modified Jacobian Inverse controller 1004 receives the Cartesian reference velocity 533 and imposes limitations on the received Cartesian reference velocity 533 during its conversion into a corresponding joint space velocity to make allowance for singularities.

A joint position and velocity limiter block 1100 receives the resultant joint velocity from the modified Jacobian Inverse controller 1004 and monitors the received joint velocity to ensure that corresponding velocity and position commands to each specific joint would not transgress angular position and velocity limitations. To prevent motions that would increase the forces exerted by the end effector 251 of the instrument 138 excessively (e.g., becoming large enough to break a suture during a suturing procedure using the instrument 138), a velocity limiter generator 1200 receives the Cartesian force "F" 404 from block 400, generates joint velocity limitations to prevent motions that would result in such excess forces being exerted by the end effector 251, and provides negative and positive joint velocity limitations 1151, 1152 to the joint position and velocity limiter block 1100.

After the joint velocity has been monitored in block 1100, and any limitations imposed, the resultant simulated slave joint velocity is output as indicated by arrow 535-1. The simulated slave joint velocity is also fed through an integrator 1010 to yield the corresponding simulated slave joint position which is also output as indicated by arrow 535-2. The simulated joint position for each specific joint is additionally routed to the joint position and velocity limiter block 1100 and the modified Jacobian inverse block 1004 as indicated in dashed lines. The simulated joint position 535-2 is routed to the modified Jacobian inverse block 1004 to enable transformation from Cartesian to joint space and routed to the position and velocity limiter block 1100 in order that the joint position and velocity limits can be imposed.

Figure 11:
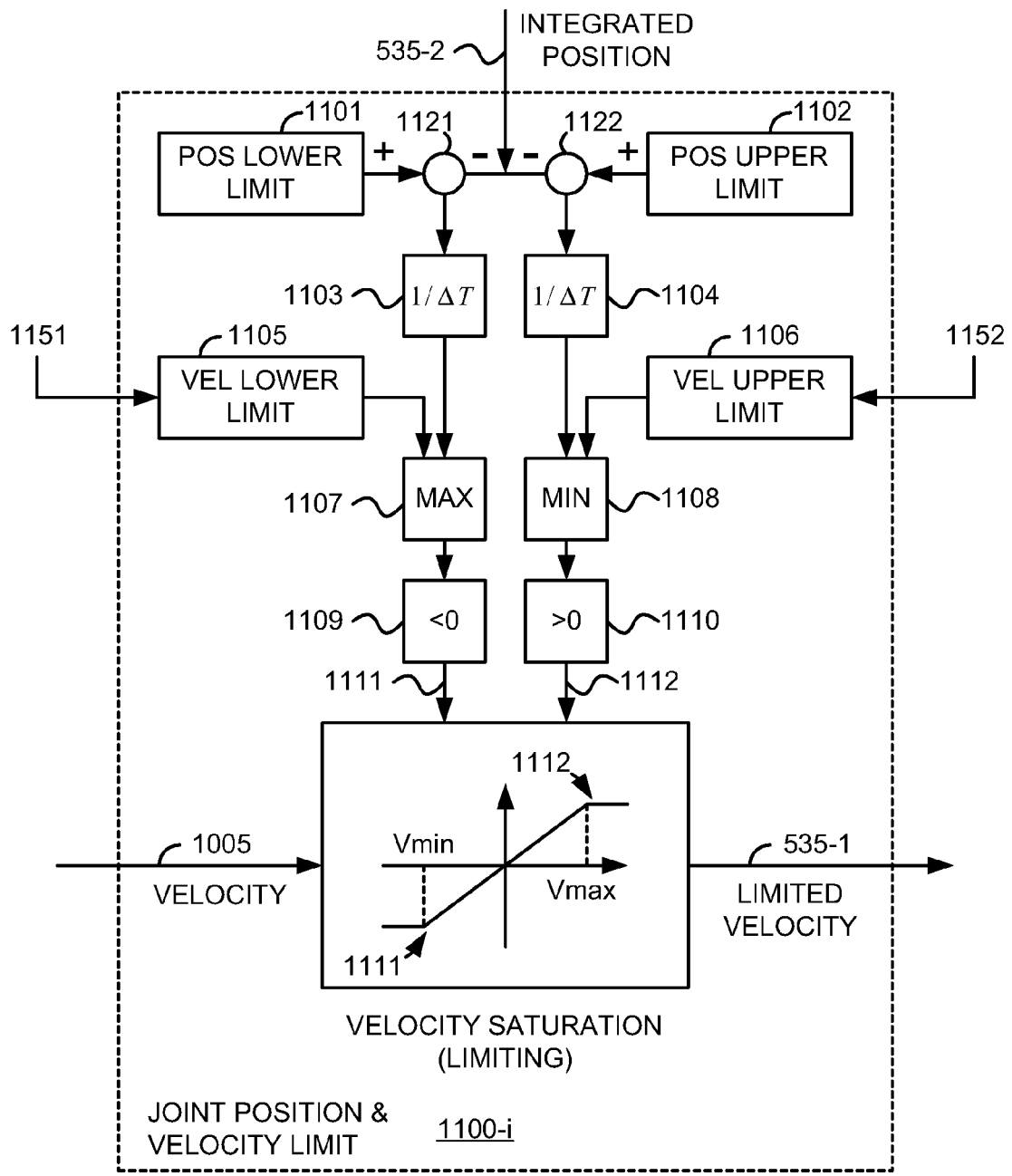
FIG. 11 illustrates a block diagram of a joint position and velocity block included in the second simulated domain block utilizing aspects of the present invention.

FIG. 11 illustrates, as an example, a block diagram of a joint position and velocity limiter block 1100-$i$ for the $i^{th}$ joint of the robotic arm assembly 128. Other joints in the robotic arm assembly 128 have similar joint position and velocity limiter blocks. The joint position and velocity limiter block 1100 is therefore comprised of the combination of all such limiter blocks for all the joints in the robotic arm assembly 128. Although inputs and outputs to the limiter block 1100-$i$ show entire vectors (i.e., 1005, 535-2, 1151, 1152, 535-1), it would be appreciated that the block 1100-$i$ only processes the $i^{th}$ component of these vectors (representing the $i^{th}$ joint).

The joint velocity input from the modified Jacobian inverse controller at 1004 is indicated by arrow 1005. The resultant velocity after having passed through the joint position and velocity limiter block 1100 is indicated by arrow 535-1 and the joint position input is indicated by arrow 535-2. Each joint for which position and velocity limits is to be imposed normally has physical limitations. Thus, the joint has a maximum position in which the arm members which are pivotally connected thereby are at a maximum angular position relative to each other. Similarly, the joint has a minimum position in which the arm members which are connected one to another thereby are at a minimum angular position relative to each other. Accordingly, the joint has an angular displacement range extending between its minimum and its maximum position. The angular limits of the joint are indicated by blocks 1101 and 1102, respectively, block 1101 indicating the minimum position and block 1102 the maximum position. Naturally, since we are dealing with a simulated domain, the limits can be chosen to suit. Accordingly, the minimum and maximum angular positions 1101, 1102 need not necessarily correspond with the actual physical positional limits of the joint, but can be chosen at any appropriate angular positions within the angular positional range capabilities of the joint.

The position input at 535-2 is normally varying continually as the surgeon manipulates the master manipulator 108 during the course of a medical procedure. The positional input 535-2 is fed to the summation junctions 1121, 1122. At the junction 1121, the angular position as input at 535-2 is compared with the positional minimum or lower limit to yield an angular value corresponding to the angular deviation of the position input 535-2 relative to the limit 1101. Thus, at 1121, an angular value equal to the difference between the angular limit and the angular position input 535-2 is determined. The angular deviation from the lower limit 1101 is then fed to a velocity determination block at 1103. The processing cycle rate of the control system is known. In this case, it is typically 1300 Hz. At 1103, the velocity which the joint needs to have to cause its position to coincide with the lower joint limit 1101 at the next processing cycle is determined. This velocity value is then routed to a decision block at 1107. Naturally, if the angular position as input at 535-2 is far removed from the lower limit 1101, the resultant velocity value derived at 1103 will be very large, and typically physically unattainable. However, as the angular deviation approaches zero, namely, where the angular position 535-2 approaches the lower limit 1101, the velocity output from 1103 becomes less than the attainable joint velocity and becomes zero where the angular position 535-2 is at the lower limit 1101.

Reference numeral 1105 represents a lower joint velocity limit which is provided by the velocity limit generator 1200 as indicated by arrow 1151 to the $i^{th}$ joint position and velocity limiter block 1100-$i$. The lower joint velocity limit is fed along with the output of the block 1103 into the decision block 1107. At 1107 the two joint velocities are compared and the larger of the two selected. It will be appreciated that the larger value is selected because we are regarding a velocity limit in a negative direction. Thus, the larger value is the same as the smaller absolute value. The selected velocity value thus determined defines the lower joint velocity limit as indicated at 1111.

It could happen that the joint is positioned beyond the positional lower limit 1101. This can occur when the medical robotic system 100 is initially setup, or where the positional limits are selectively changed, for example. In such a case, it is desirable to cause the joint position to return to within the range set by the upper and lower limits at 1101, 1102, respectively. For the lower angular position limit, this is achieved by the block 1109. What is achieved by the block 1109 is a constant curbing of positional movement beyond the lower limit. Thus, as the surgeon manipulates the master, movements causing the angular position of the joint to move toward the limit are permitted, but once such movement has taken place, the joint is restricted to its new position closer to the limit. The process is maintained until the joint position is within the range set by the values at 1101, 1102, respectively.

It will be appreciated that a maximum velocity, as indicated by reference numeral 1112 is determined in a similar fashion as the minimum velocity using right-side counterparts (i.e., node 1122 and blocks 1104, 1106, 1108, 1110). In this case, reference numeral 1106 represents an upper joint velocity limit which is also provided by the velocity limit generator 1200 as indicated by arrow 1152 to the $i^{th}$ joint position and velocity limiter block 1100-$i$.

Figure 12:
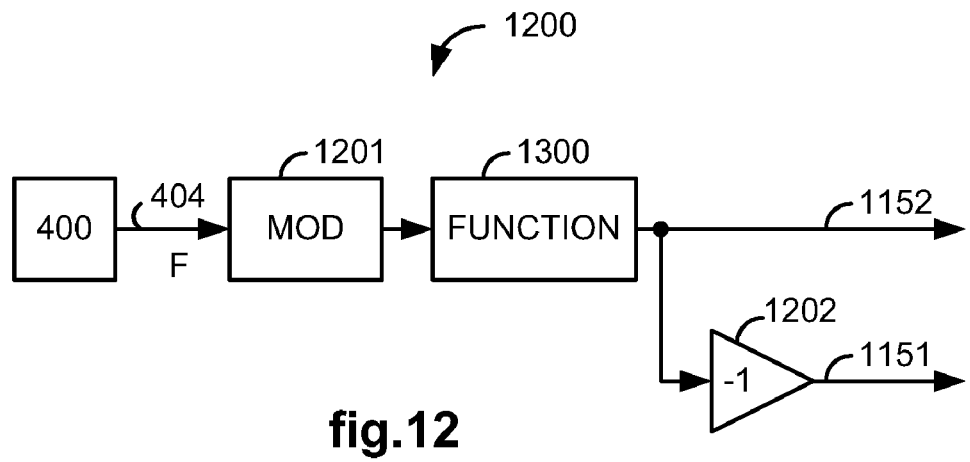
FIG. 12 illustrates a block diagram of a first velocity limit generator included in the second simulated domain block utilizing aspects of the present invention.

FIG. 12 illustrates, as an example, a block diagram of a first embodiment of the velocity limit generator 1200. A modulus block 1201 receives the Cartesian force "F" 404 and calculates its magnitude $|\vec{F}|$ (also referred to as "modulus") according to equation (8) above. A function block 1300 receives the magnitude $|\vec{F}|$ and generates a joint velocity limit 1152 according to a function of the magnitude $|\vec{F}|$. Since the output of the function block 1300 is always positive, its output sets the velocity upper limit 1152. An inverter 1202 is provided to generate the negative value of the joint velocity limit (i.e., the lower velocity limit 1151) as shown.

Figure 13:
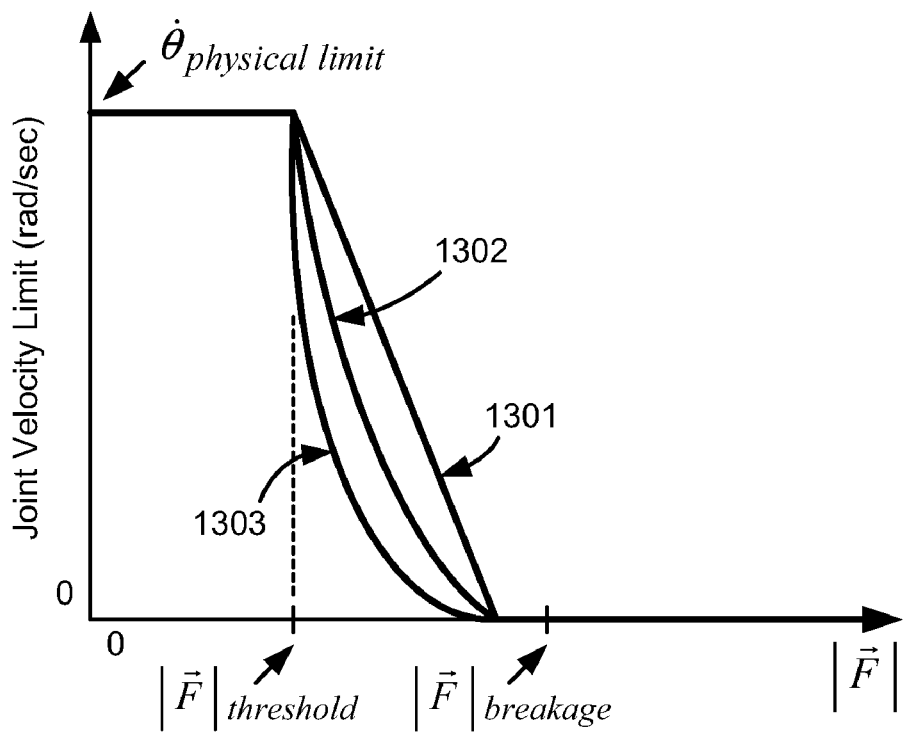
FIG. 13 illustrates exemplary functions useful in generating joint velocity limits in the first velocity limit generator included in the second simulated domain block utilizing aspects of the present invention.

FIG. 13 illustrates, as examples, exemplary functions that may be used in the function block 1300, wherein first, second, third velocity limiting functions 1301, 1302, 1303 are each characterized by their values of the joint velocity limit being based upon a physical joint velocity limit "$\dot{\theta}_{physical\ limit}$" until the magnitude of the force $|\vec{F}|$ exceeds a threshold value $|\vec{F}|_{threshold}$. At that point, the joint velocity limit decreases linearly for the first function 1301, polynomially for the second function 1302, and exponentially for the third function 1303 to the value "0". For each function, the value "0" is reached before the magnitude of the force $|\vec{F}|$ reaches a breakage force $|\vec{F}|_{breakage}$ which corresponds to a force magnitude which would be considered excessive, such as the force that would break a suture. The type of function used (i.e., the first, second, third, or other velocity limiting function) depends on user preference. For example, some users may find the linear function 1301 to be too gradual at its transitions and therefore, they may prefer a more marked transition toward a full stop such as the polynomial and exponential functions 1302, 1303 as they approach zero.

Figure 14:
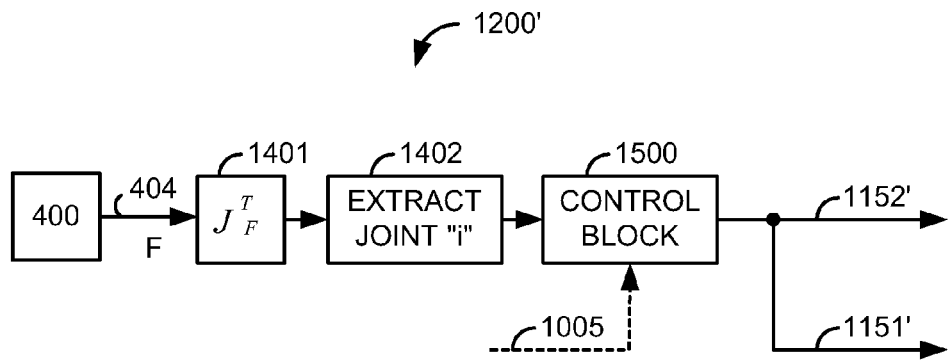
FIG. 14 illustrates a block diagram of a second velocity limit generator included in the second simulated domain block utilizing aspects of the present invention.

FIG. 14 illustrates, as an example, a block diagram of a second embodiment of the velocity limit generator 1200 (which is designated as 1200' to differentiate it from the first embodiment described in reference to FIG. 12). A kinematic mapping block 1401 receives the Cartesian force "F" 404 and generates corresponding torque values for joints of the robotic arm assembly 128 that would cause the end effector 251 to exert the Cartesian force "F" 404. An extractor 1402 extracts the torque for the $i^{th}$ joint of the robotic arm assembly 128 and passes it to a control block 1500 for processing such as described in reference to FIG. 15.

Figure 15:
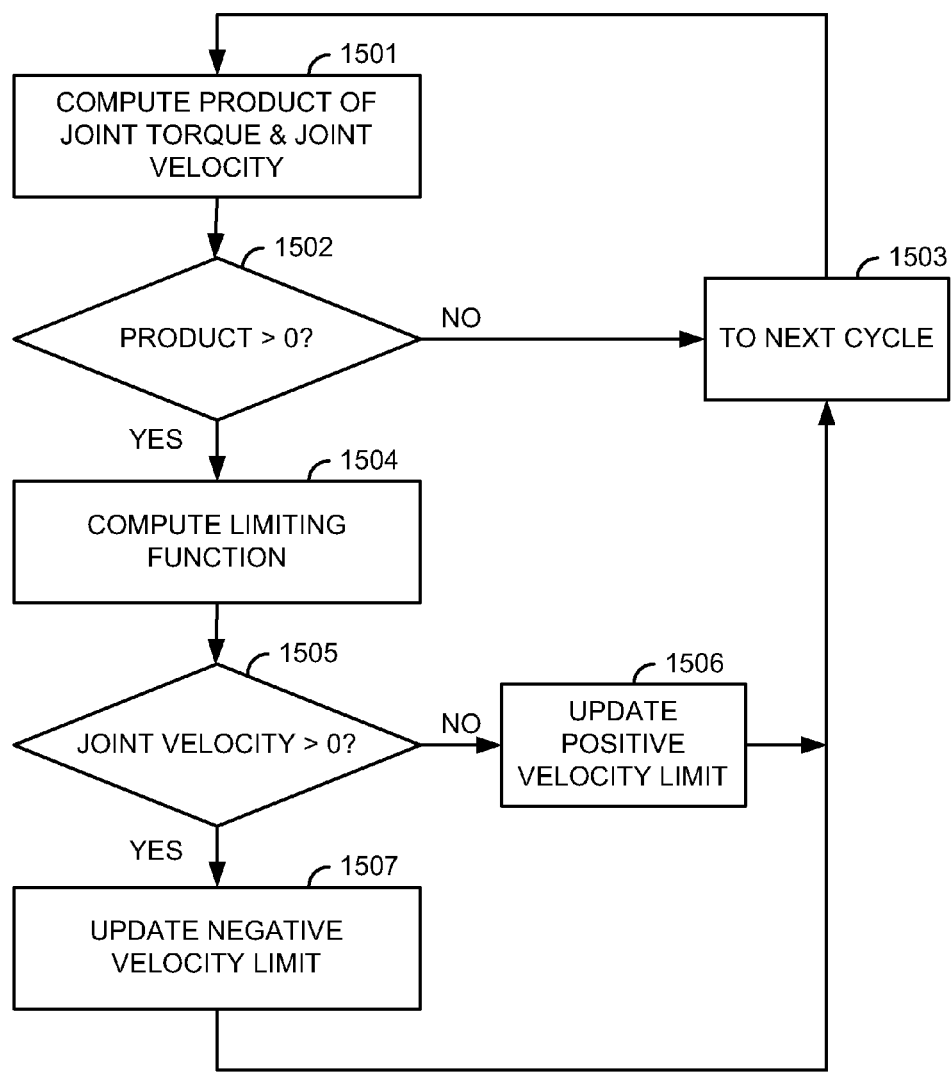
FIG. 15 illustrates a flow diagram of a method for generating velocity limits in the second velocity limit generator included in the second simulated domain block utilizing aspects of the present invention.

FIG. 15 illustrates, as an example, a flow diagram of a method implemented in the control block 1500. In 1501, a product of the joint torque "$\tau$" and joint velocity "$\dot{\theta}$" is calculated. In 1502, a determination is made whether the calculated product is greater than zero. If the determination in 1502 is NO, then the joint torque and joint velocity are in opposing directions and an excessive force is not being threatened at the time. Therefore, the initially set velocity limits are not updated at this time and the method proceeds to 1503 where it jumps back to 1501 to process 1501-1507 for the next cycle. The initially set velocity limits may be determined in this case by physical constraints of the robotic arm assembly 128.

Figure 16:
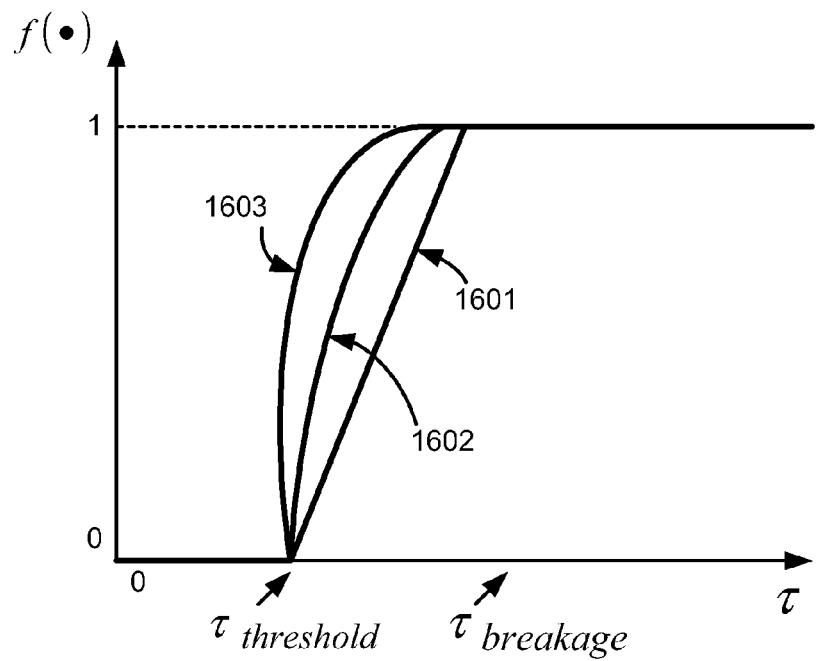
FIG. 16 illustrates exemplary functions useful in generating joint velocity limits in the second velocity limit generator included in the second simulated domain block utilizing aspects of the present invention.

On the other hand, if the determination in 1502 is YES, then in 1504, a value "$f(\cdot)$" is computed from a velocity limiting function, such as one of the functions depicted in FIG. 16, wherein first, second, third velocity limiting functions 1601, 1602, 1603 are each characterized by their values of "$f(\cdot)$" being zero until the torque "$\tau$" exceeds a threshold value $\tau_{threshold}$. At that point, the value "$f(\cdot)$" increases linearly for the first function 1601, polynomially for the second function 1602, and exponentially for the third function 1603 to the value "1". For each function, the value "1" is reached before the torque "$\tau$" reaches a breakage torque $\tau_{breakage}$ which corresponds to a torque which would be considered excessive, such as a torque which would cause a force exerted by the end effector 251 that would break a suture. The type of function used (i.e., the first, second, third, or other velocity limiting function) depends on user preference. For example, some users may find the linear function 1601 to be too gradual at its transitions and therefore, they may prefer a more marked transition such as the polynomial and exponential functions 1602, 1603 as they approach the value "1".

In 1505, a determination is made whether the joint velocity is greater than zero. If the determination in 1505 is NO, then in 1506, the positive velocity limit 1152' is updated according to the following equation:

New Positive Velocity Limit=$[1-f(\cdot)]\times$[Initial Positive Velocity Limit] (11)

On the other hand, if the determination made in 1505 is that the joint velocity is less than or equal to zero, then in 1507, the negative velocity limit 1151' is updated according to the following equation:

New Negative Velocity Limit=$[1-f(\cdot)]\times$[Initial Negative Velocity Limit] (12)

and the method then proceeds to 1503 where it jumps back to 1501 to process 1501-1507 for the next cycle.

In addition to preventing excessive forces from being exerted by the end effector 251, the control system 300 also warns the surgeon when excessive forces are being applied by the end effector. As previously explained in reference to FIG. 3, when the simulated velocity or position generated by the simulated domain 308 does not match the commanded velocity or position, then a resistance (e.g., haptic feedback) indicating the non-match is provided to the surgeon on the master manipulator 108.

Alternatively, or in addition to, haptic feedback indicating the excessive force, visual, auditory and/or vibratory warnings may also be provided. For example, in some embodiments, resultant forces from block 400 may be indicated in an alternative manner to the surgeon. For example, the total force may be presented in the form of a bar graph shown on the display, typically beyond a border of the displayed image from the image capture device. Alternatively, the resulting forces applied against the slave manipulator of each robotic arm assembly may be graphically shown as a force vector, either outside the image border on the display, or overlaid over the slave structure in the displayed image. Still further presentation alternatives are possible, including the use of false colors (for example, changing the color of a slave component to yellow and then red as the component approaches and then reaches its maximum force capability), or audibly indicating the force on the slave structure with a tone which increases in pitch and/or volume as forces increase. Additional tactile representations of force may be employed, for example, using heat to indicate force or an inertial actuator which, for example, vibrates with increasing speed or amplitude as forces increase. Such inertial actuators may apply apparent forces to an input device where no linkage supports the input device relative to a fixed frame of reference, for example, when using exoskeletal gloves supported by the surgeon's arm.

In general, non-visual information such as force which is sensed by the slave may be presented in corresponding non-visual formats (i.e., force reflecting master/slave arrangements), or in an alternative non-visual form (for example, force presented as sounds or heat). Non-visual information sensed by the slave may also be displayed to the Surgeon in a visual format, such as using a bar graph or force vector, as described above. As used herein, non-visual information includes tactile sense information (including force, pressure, vibration, texture, heat, and the like), sound information (which may be sensed using a microphone of the slave), smell/taste (as may be sensed using a chemical or biochemical sensor of the slave), and the like.

Although the various aspects of the present invention have been described with respect to a preferred embodiment, it will be understood that the invention is entitled to full protection within the full scope of the appended claims.

What is claimed is:
1. A system comprising:
a robotic surgical instrument having an end effector;
an input device that generates commanded movement of the end effector; and a master/slave control system coupled to the input device and to the end effector,
wherein the master/slave control system receives the commanded movement of the end effector, and
wherein in response to the commanded movement of the end effector, the master/slave control system restricts a velocity of the commanded movement to a determined reduced velocity if the velocity of the commanded movement would cause a suture held by the end effector to break.

2. The system of claim 1, wherein the master/slave control system further comprises:
a warning system, wherein the warning system generates a warning if the velocity of the commanded movement would cause the suture held by the end effector to break.

3. The system of claim 2, wherein the warning includes visual information.

4. The system of claim 2, wherein the warning includes non-visual information.

5. The system of claim 4, wherein the non-visual information includes at least one of tactile sense information and sound information.

6. The system of claim 1, wherein the master/slave control system further comprises:
a simulated slave processing unit,
wherein the simulated slave processing unit receives a desired Cartesian velocity signal and a desired Cartesian position signal that are based on the commanded movement of the end effector, and
wherein the simulated slave processing unit generates a physical slave joint velocity command and a physical slave joint position command so that the velocity of the commanded movement is limited to the determined reduced velocity if the velocity of the commanded movement would cause the suture held by the end effector to break.

7. The system of claim 6, wherein the simulated slave processing unit further comprises:
a Cartesian velocity limiter coupled to receive a Cartesian force signal,
wherein the Cartesian force signal represents a force exerted by the end effector, and
wherein the Cartesian velocity limiter generates a limited Cartesian reference velocity signal that limits a component of the desired Cartesian velocity in a direction of the Cartesian force; and
a simulator coupled to the Cartesian velocity limiter to receive the limited Cartesian reference velocity signal,
wherein the simulator generates a simulated joint velocity and a simulated joint position, and
wherein the simulator limits the simulated joint velocity to a determined reduced velocity if the velocity of the commanded movement would cause the suture held by the end effector to break.

8. The system of claim 7, wherein the simulated slave processing unit further comprises:
a post-processor coupled to receive the simulated joint velocity and the simulated joint position from the simulator,
wherein the post-processor filters the simulated joint velocity and the simulated joint position, and
wherein the post-processor generates the physical slave joint velocity command and the physical slave joint position command.

9. The system of claim 6, wherein the simulated slave processing unit further comprises:
a simulator coupled to receive the desired Cartesian reference velocity signal and coupled to receive a Cartesian force signal,
wherein the Cartesian force signal represents a force exerted by the end effector,
wherein the simulator generates a simulated joint velocity and a simulated joint position, and
wherein the simulator limits the simulated joint velocity to a determined reduced velocity if the velocity of the commanded movement would cause the suture held by the end effector to break.

10. The system of claim 9, wherein the simulated slave processing unit further comprises:
a post-processor coupled to receive the simulated joint velocity and the simulated joint position from the simulator,
wherein the post-processor filters the simulated joint velocity and the simulated joint position from the simulator, and
wherein the post-processor generates the physical slave joint velocity command and the physical slave joint position command.

11. The system of claim 9, wherein the simulator further comprises:
a modified Jacobian inverse controller coupled to receive the desired Cartesian reference velocity signal,
wherein the modified Jacobian inverse controller imposes limitations on the desired Cartesian reference velocity during conversion into a corresponding joint space velocity to make allowance for singularities, and
wherein the modified Jacobian inverse controller generates a resultant joint velocity; and
a velocity limit generator coupled to receive the Cartesian force signal,
wherein the velocity limit generator generates a joint velocity lower limit and a joint velocity upper limit.

12. The system of claim 11 wherein the simulator further comprises:
a joint position and velocity limiter coupled to receive the resultant joint velocity from the modified Jacobian controller and coupled to receive the joint velocity lower and upper limits from the velocity limit generator,
wherein the joint position and velocity limiter generates the simulated joint velocity and the simulated joint position.

13. A method comprising:
receiving, from an input device, commanded movement of an end effector of a robotically manipulated surgical instrument; and
controlling robotic manipulation of the surgical instrument, in response to the commanded movement of the end effector, to restrict a velocity of the commanded movement to a determined reduced velocity if the velocity of the commanded movement would cause a suture held by the end effector to break.

14. A method comprising:
receiving, from an input device, commanded movement of an end effector of a robotically manipulated surgical instrument;
controlling robotic manipulation of the surgical instrument, in response to the commanded movement of the end effector, to restrict a velocity of the commanded movement to a determined reduced velocity if the velocity of the commanded movement would cause a suture held by the end effector to break; and outputting an indication of a force created by the commanded movement if the velocity of the commanded movement would cause the suture held by the end effector to break.

15. The method of claim 14, wherein the outputting includes outputting visual information.

16. The method of claim 14, wherein the outputting includes outputting non-visual information.

17. The method of claim 16, wherein the non-visual information includes at least one of tactile sense information and sound information.

18. The method of claim 14, wherein the outputting further comprises:

displaying a representation of the force on a display device.

* * * * *